United States Patent [19]

Demuth

[11] Patent Number: 4,499,902

[45] Date of Patent: Feb. 19, 1985

[54] RECEIVER DEVICE FOR A MULTI-ELEMENT ULTRASONIC PROBE ECHOGRAPH AND ECHOGRAPH EQUIPPED IN THIS WAY

[75] Inventor: Dietmar Demuth, Schwerte, Fed. Rep. of Germany

[73] Assignee: Thomson-CSF, Paris, France

[21] Appl. No.: 355,576

[22] PCT Filed: Jun. 23, 1981

[86] PCT No.: PCT/FR81/00082

§ 371 Date: Feb. 22, 1982

§ 102(e) Date: Feb. 22, 1982

[87] PCT Pub. No.: WO82/00061

PCT Pub. Date: Jan. 7, 1982

[30] Foreign Application Priority Data

Jun. 23, 1980 [DE] Fed. Rep. of Germany ....... 3023386

[51] Int. Cl.³ .............................................. A61B 10/00
[52] U.S. Cl. ....................................... 128/660; 73/625
[58] Field of Search ............................... 128/660, 661; 73/625–626

[56] References Cited

U.S. PATENT DOCUMENTS

| | | | |
|---|---|---|---|
| 4,019,169 | 4/1977 | Takamizawa | 367/105 |
| 4,159,462 | 6/1979 | Rocha et al. | 367/97 |
| 4,173,007 | 10/1979 | McKeighen et al. | 367/11 |
| 4,227,417 | 10/1980 | Glenn | 128/660 X |
| 4,257,271 | 3/1981 | Glenn | 128/660 X |
| 4,267,584 | 5/1981 | McKeighen et al. | 128/660 X |
| 4,317,370 | 3/1982 | Glenn | 128/660 X |

*Primary Examiner*—Kyle L. Howell
*Assistant Examiner*—Francis J. Jaworski
*Attorney, Agent, or Firm*—Roland Plottel

[57] ABSTRACT

A receiver device for a multi-element ultrasonic probe echograph comprises for each transducer element (11 to 1N) of the probe (1) a delay line (71 to 7N) controlled by digital time delay circuits (31 to 3N) which supply control signals via digital input-output logics (51 to 5N) controlled by an operating control circuit (2), which transmits signals (S1 to SN) to the delay circuits (31, 3N) by a single clock (6) and by a single input-output control circuit (4).

3 Claims, 2 Drawing Figures

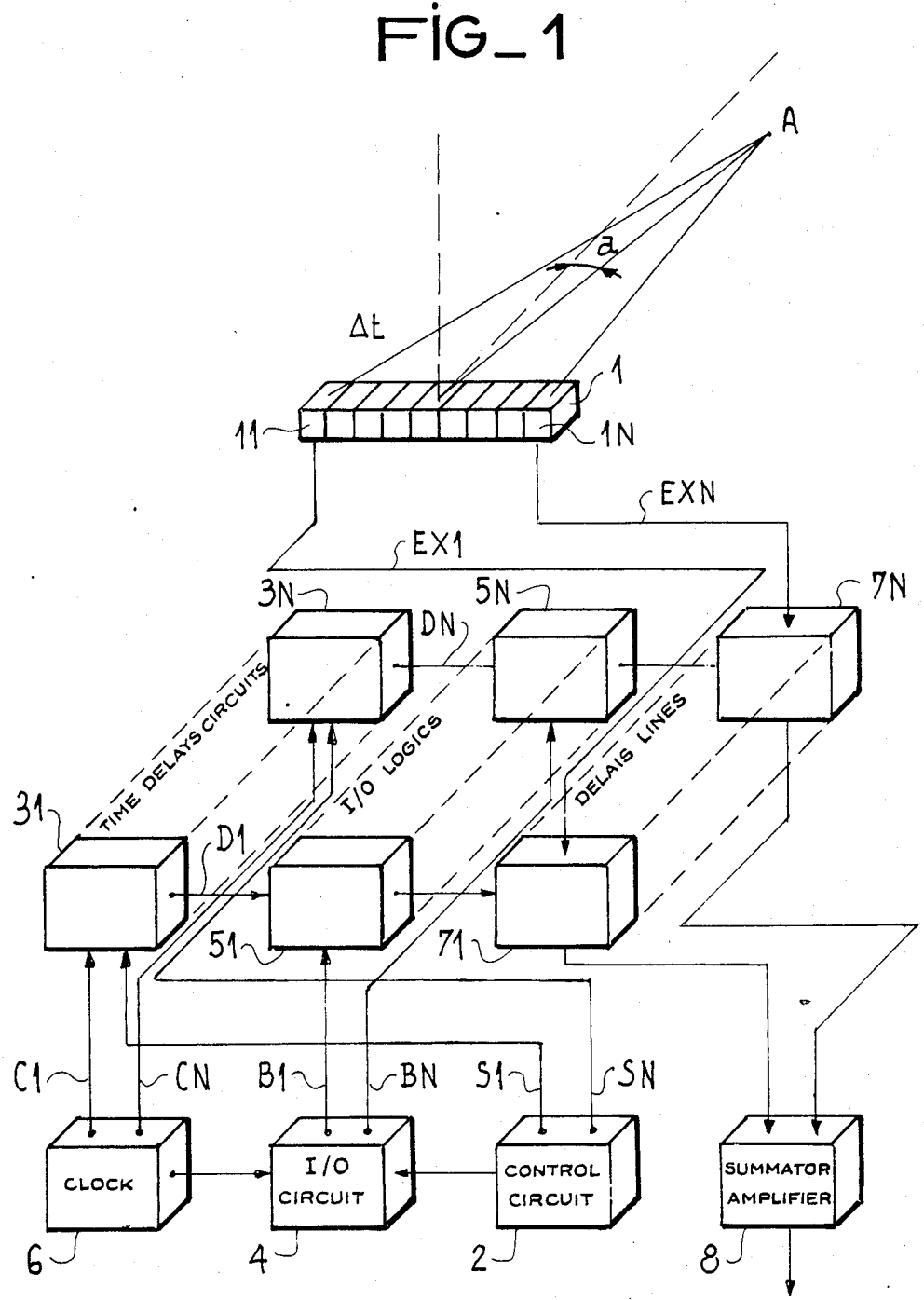

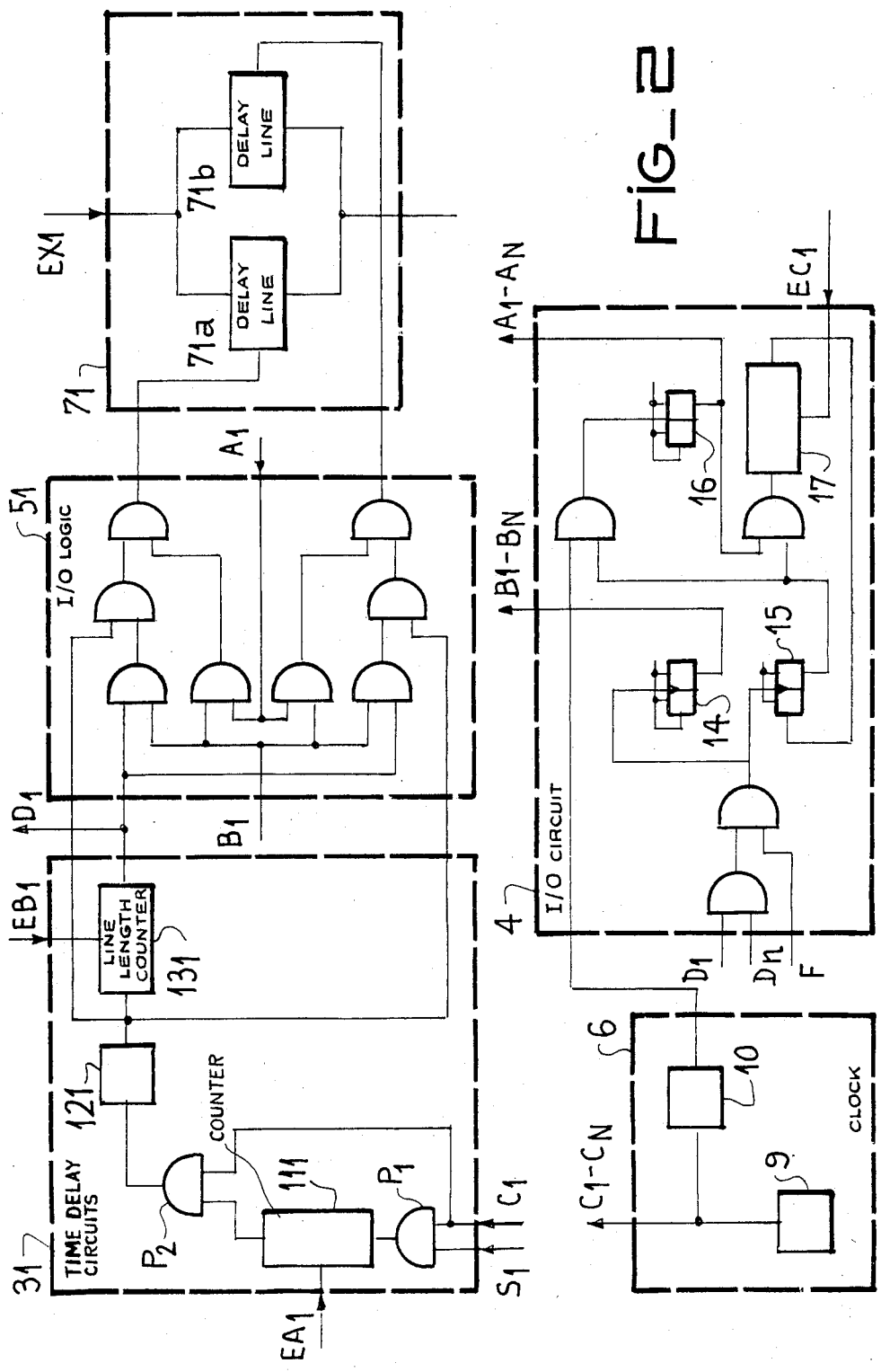
FIG_2

RECEIVER DEVICE FOR A MULTI-ELEMENT ULTRASONIC PROBE ECHOGRAPH AND ECHOGRAPH EQUIPPED IN THIS WAY

BACKGROUND OF THE INVENTION

The present invention relates to a receiver device for a multi-element ultrasonic probe echograph and an echograph equipped in this way. It more particularly relates to the field of ultrasonic medical diagnosis. Piezoelectric transceiver means are known from the prior art. These devices or piezoelectric probes make it possible to transmit ultrasonic waves when piezoelectric crystals are excited by electric pulses at a predetermined transmission frequency. The transmitted waves are propagated in the medium of which it is desired to form an image. They are partly reflected by acoustic impedance differences between the nonhomogeneous media encountered. The reflections are called echos. They are pressure waves which the piezoelectric probe translates into electric pulses called response echo signals. As the ultrasonic wave has a certain propagation velocity in the medium, each echo is received after transmission at a time which is dependent on the distance from the obstacle which reflects it. For carrying out automatic scans of the inside of a body by means of ultrasonics, it has been proposed to transmit ultrasonic waves by multi-element probes. A plurality of piezoelectric transducer elements are distributed in such probes. On transmission, the ultrasonic beam is formed by exciting each transducer element in phase relationship with its neighbours.

In a first construction called a linear scanning probe, the latter comprises N adjacent elements. At a given time, the ultrasonic beam is produced by exciting P adjacent elements taken from among the N elements of the probe. By applying predetermined time delays which vary from one element to the next, it is possible to focus the ultrasonic energy of the beam at a predetermined point, called the examination focus. By displacing the addressing of electrical signals relative to the series of P adjacent elements, it is possible to carry out a linear scan of the examination plane.

In a second construction called a sector scanning probe, the time delay law applied to each transducer element of the probe is such that the focus obtained can be displaced in an angular manner about the probe axis.

On reception, each echo signal received is transmitted to the processing device of the signal across a regulatable delay line by an electronic control circuit. In order to obtain high operating dynamics it is necessary for each delay line to be able to supply delays which are as short as possible and delays which exceed one second. At all times, the delay laws applied to the delay line elements must be such that the various signals transmitted to the processing device correspond at a given time to the same echo reflected by the obstacle.

It is known to use charge coupled devices or CCD's for obtaining these delay lines. In such a device, any signal supplied to the input is progressively transmitted at a given input analysis speed and at a passage rate which are determined by a clock signal able to vary in wide frequency ranges, which determine the dynamics and therefore the characteristics of the ultrasonic beam received.

To obtain different delays for each delay line channel, the clock frequency is diversified as a function of the reception angle and consequently the transducer element in question. The regulation of the clock frequencies must take place rapidly and with a given precision. The necessary electronic circuits for such a construction considerably increase the cost of the examination equipment. This is particularly the case when frequency regulation takes place in a synthesizer by means of an oscillator controlled by the VCO voltage. Another problem encountered with delay line service devices is the thermal drift. Finally, it is also necessary to compensate the voltage dependence.

BRIEF SUMMARY OF THE INVENTION

An advantage of the present invention is that it is able to relatively inexpensively improve the regulation or control precision and the overall stability in a receiver device of the type referred to hereinbefore.

According to the invention, this problem is solved in that the delay lines comprise in either case of the linear scanning or phrased array probe at least one charge transfer element and are connected to a digital input-output logic existing for each delay line. The logic systems are in each case connected on the one hand to a digital time delay circuit and on the other to a digital input-output control common to all the delay lines. Hence a single clock source at a single frequency may govern echo data acquisition into the charge transfer elements used as anlog memories, with the delay function provided by accessory time delay control circuits governing the onset of loading into transfer element storage.

BRIEF DESCRIPTION OF THE DRAWINGS

The invention is described in greater detail hereinafter relative to non-limitative embodiments and with reference to the attached drawings, wherein show:

FIG. 1 a diagram of the circuit according to the invention.

FIG. 2 a constructional variant of the circuit of FIG. 1.

DETAILED DESCRIPTION OF THE PREFERRED EMBODIMENTS

In FIG. 1, a probe 1 comprises a plurality of transducer elements 11 depicted as a phased array which, when excited by a pulse generator having the same number of channels as there are transducers, transmits an ultrasonic wave focused at point A. This wave constitutes a beam inclined at an angle a with the perpendicular to the linear probe. According to the delay law of the signal applied to each transducer element, angle a and the distance from point A to the centre of the probe varies. The per se known probe excitation pulse generator is not shown in the drawing. The wave concentrated at point A is retransmitted in part by the latter and returns at one end to transducer elements 11 in the form of an ultrasonic echo. In response to the ultrasonic wave which it receives, the transducer element produces a signal called an echo signal EX1 to EXN, which is transmitted to a summator-amplifier 8 across a delay line 71 to 7N. The delays on the delay line are controlled by a time delay circuit 31 to 3N. Each circuit 31 to 3N receives on the one hand a frequency control C1 to CN from a clock 6 and on the other an operating control S1 to SN from an operating control circuit 2. Each delay line 71 to 7N receives the control D1 to DN from the time delay circuits 31 to 3N via input-output logics 51 to 5N. Each of the logics 51 to 5N receives a control B1 to BN from an input-output control circuit 4.

FIG. 2 shows a special embodiment of the invention. FIG. 2 shows a data acquisition channel receiving an echo signal X1 transmitted to the summator-amplifier 8. A channel comprises a delay line 71, an input-output logic 51, a time delay circuit 31 which receives the controls from the not shown operating control circuit 2, an input-output control circuit 51 and a clock 6.

The operating control circuit which is any per se conventional memory of cyclical readout supplies signals EA1, EB1 and EC1 respectively to circuits 31 and 4. The operating control gives the so-called starting signal S1 to SN after suppling the transmission pulse. Gate P1 allows clocking to counter 111 when start signal S1 is received. In this way, a delay time counter 111 is operated. Counter 111 is loaded by its input EA1 to an initial value which is counted down to the zero value when it transmits a zero signal and therefore serves a delay function. This signal, formed with signal C1 supplied by clock 6 in an AND gate P2, transmits the clock signal C1 to a divider 121. Divider 121 divides the frequency of the clock signal C1 by a factor Z. This division is a well-known technique for providing clocking at different rates to different circuit components from a single clock source; hence Z is a choice of design in each case. The divided frequency signal is transmitted to a line length counter 131 brought by control 2 and its input EB1 to a predetermined value associated with duration of echo signal EX1. As a function of the position of an electronic switch, counter 131 permits the timing of measured echo signal EX1 via logic 51 in delay line 71. In the present case, the electronic switch is constituted by a flip-flop in the input-output control circuit 4. Flip-flop 14 produces a signal B1 to BN transmitted to the input-output logic 51. Signal B1 is formed by signal A1 supplied by flip-flops 15 and 16 via four AND gates.

After stopping the line length counter 131, the useful signal is completely recorded in one of the CCD's 71A or 71B of delay line 71. The timing system then stops operating. It is only when all the line length counters 131 to 13N have been reset that signals D1 to DN are applied to an N-input AND gate within circuit 4 and so it is possible to extract the useful information by applying the release signal F generated by circuit 2. When all the line counters 131 are again at zero an electronic switching element, in the present case a flip-flop 15, is reversed and remains in this state whilst an output counter is operating. During this time, the CCD's which previously received the useful signal are emptied in parallel. When they are all empty, the timing system is stopped. Circuit 51 acts as a two-state device to govern input to and output from the alternative CCD storage memories 71A and 71B.

In order to manage all the channels, it is possible with switch 14 and switch 15 to free one or other of the CCD groups A or B, i.e. to free CCD's 71A to 7NA and then prepare the other group for the input of a new useful signal 71B to 7NB. Thus, it is possible to start a new input cycle as soon as the counters have been returned to the initial state. The output counter 17 is driven by the output of divide-down 10 and thus monitors the unloading of the said CCD group and is not returned to this initial state until the output has been completed.

Another switch in the input-output control 4, e.g. a flip-flop 16 ensures the pulses at the output. It switches on the descending front of the signal coming from the master frequency 9 of clock 6. The frequency of this clock has been divided by factor Z/2 in a divider 10. Thus, it is ensured that no matter what the reversal time of electronic switch, the timing of the useful signal takes place on a state change of the clock signal and not at the state change time of switch 15. The use of the clock frequency signal divided by a factor Z/2 ensures that the inaccuracy of the delay time will only be approximately one cycle of the master frequency 9.

The use of two CCD's 71A and 71B is advantageous in that whilst feeding in a preceding useful information, it is possible to simultaneously feed in a new useful information after consequently delaying the start of recording. This provides an additional advantage compared with the known timing at a variable clock frequency having only a single CCD per channel. Thus, the clock frequency for feeding out the preceding useful information is the same as that necessary for feeding in the following useful information. Thus, a phase error would appear during the summation of the following useful information.

Charge transfer elements other than CCD's can be used. Existing technologies make it possible to bury in a charge transfer device a channel which facilitates the transfer of charges to the control means. Peristaltic charge coupled devices (PCCD) are well known for their operating speed (up to 100 megahertz). They are applied in the present invention, where they make it possible to obtain faster information flows.

What is claimed is:

1. A receiver device for a multielement ultrasonic probe echograph comprising a probe having a plurality of transducer elements (11, 1N), a corresponding number of CCD units (71, 7N) respectively interconnected between the transducer elements and a summator means (8), one clock means (9) and, for each CCD unit, a delay time counter means (111) connected between said clock means and a respective gate means connected to a control input of said CCD unit and furthermore a corresponding line length counter (131) downstream of said gate means, outputs of all said line length counters being connected to validation means of read control means (4) of the CCD devices previously operated in record mode.

2. A receiver device according to claim 1 wherein each CCD unit comprises at least two CCD devices in parallel relationship between the corresponding transducer element and said summator means (8) and wherein means (4, 51–5N) are provided for alternately controlling one of a CCD device in load-record mode to receive a useful echo signal corresponding to an emission-reception, sequence from said transducer element and other CCD device in unload-read mode to supply said summator means with a previously recorded useful signal corresponding to a previous emission-reception sequence.

3. A receiver device according to claim 1 comprising for each CCD unit a digital divider (121) interconnected between said gate means and said CCD unit.

* * * * *